US00PP18301P2

(12) United States Plant Patent
Meszaros

(10) Patent No.: US PP18,301 P2
(45) Date of Patent: Dec. 11, 2007

(54) *IPOMOEA* PLANT NAMED 'IP059'

(50) Latin Name: *Ipomoea batatas*
Varietal Denomination: IP059

(75) Inventor: Debra Meszaros, Riverhead, NY (US)

(73) Assignee: Advanced Plant Technologies LLC, Riverhead, NY (US)

( * ) Notice: Subject to any disclaimer, the term of this patent is extended or adjusted under 35 U.S.C. 154(b) by 0 days.

(21) Appl. No.: 11/438,527

(22) Filed: May 22, 2006

(51) Int. Cl.
*A01H 5/00* (2006.01)

(52) U.S. Cl. ..... Plt./258

(58) Field of Classification Search ..... None
See application file for complete search history.

(56) References Cited

U.S. PATENT DOCUMENTS

PP15,028 P3 * 7/2004 Pecota et al. ..... Plt./258

* cited by examiner

*Primary Examiner*—Wendy C. Haas
(74) *Attorney, Agent, or Firm*—C. A. Whealy

(57) ABSTRACT

A new and distinct cultivar of *Ipomoea* plant named 'IP059', characterized by its compact and mounding growth habit; freely branching plant habit; relatively small deeply dissected light green-colored foliage; and pink-colored flowers.

2 Drawing Sheets

Botanical designation: *Ipomoea batatas.*
Cultivar denomination: 'IP059'.

BACKGROUND OF THE INVENTION

The present invention relates to a new and distinct cultivar of *Ipomoea,* botanically known as *Ipomoea batatas,* also known by the trade name Dwarf Marguerite Improved and hereinafter referred to by the name 'IP059'.

The new *Ipomoea* is a product of a planned breeding program conducted by the Inventor in Riverhead, N.Y. The objective of the breeding program is to create new compact *Ipomoea* cultivars with attractive foliage shape and coloration.

The new *Ipomoea* originated from a cross-pollination made by the Inventor on Nov. 11, 2001 in Riverhead, N.Y. of the *Ipomoea batatas* cultivar Blackie, not patented, as the female, or seed, parent with a pollen mixture collected from plants of the *Ipomoea batatas* cultivars Marguerite and Lady Fingers, both not patented, as the male, or pollen, parent. The new *Ipomoea* was discovered and selected by the Inventor as a single flowering plant within the progeny of the stated cross-pollination in a controlled environment in Riverhead, N.Y. on Jul. 14, 2004. The selection of this plant was based on its compact growth habit and attractive foliage shape and coloration.

Asexual reproduction of the new *Ipomoea* by terminal cuttings in a controlled environment in Riverhead, N.Y. since February, 2005, has shown that the unique features of this new *Ipomoea* are stable and reproduced true to type in successive generations.

SUMMARY OF THE INVENTION

The cultivar IP059 has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'IP059'. These characteristics in combination distinguish 'IP059' as a new and distinct cultivar of *Ipomoea:*

1. Compact and mounding growth habit.
2. Freely branching plant habit.
3. Relatively small deeply dissected light green-colored foliage.
4. Pink-colored flowers.

Plants of the new *Ipomoea* can be compared to plants of the female parent, the cultivar Blackie. Plants of the new *Ipomoea* differ from plants of the cultivar Blackie in the following characteristics:

1. Plants of the new *Ipomoea* are much more compact and less vigorous than plants of the cultivar Blackie.
2. Plants of the new *Ipomoea* have shorter internodes than plants of the cultivar Blackie.
3. Plants of the new *Ipomoea* have smaller leaves than plants of the cultivar Blackie.
4. Plants of the new *Ipomoea* have light green-colored foliage whereas plants of the cultivar Blackie have purple-colored foliage.

Plants of the new *Ipomoea* can be compared to plants of the pollen parents, the *Ipomoea batatas* cultivars Marguerite and Lady Fingers. Plants of the new *Ipomoea* differ primarily from plants of the cultivars Marguerite and Lady Fingers in leaf shape.

Plants of the new *Ipomoea* can also be compared to plants of the cultivar Sweet Carolina Light Green, disclosed in U.S. Plant Pat. No. 15,028. In side-by-side comparisons conducted in Riverhead, N.Y., plants of the new *Ipomoea* and the cultivar Sweet Carolina Light Green differed in the following characteristics:

1. Plants of the new *Ipomoea* were more compact and less vigorous than plants of the cultivar Sweet Caroline Light Green.

2. Plants of the new *Ipomoea* had smaller leaves than plants of the cultivar Sweet Caroline Light Green.
3. Plants of the new *Ipomoea* produced flowers whereas plants of the cultivar Sweet Carolina Light Green did not produce flowers.

BRIEF DESCRIPTION OF THE PHOTOGRAPHS

The accompanying colored photographs illustrate the overall appearance of the new *Ipomoea,* showing the colors as true as it is reasonably possible to obtain in colored reproductions of this type. Colors in the photographs may differ slightly from the color values cited in the detailed botanical description which accurately describe the colors of the new *Ipomoea.*

The photograph on the first sheet comprises a side perspective view of a typical plant of 'IP059' grown in a container.

The photograph on the second sheet comprises a close-up of typical leaves of 'IP059' (left) and 'Blackie' (right).

DETAILED BOTANICAL DESCRIPTION

The photographs and following observations, measurements and values describe plants grown in Riverhead, N.Y. in a polyethylene-covered greenhouse during the spring and summer under conditions which closely approximate commercial production. During the production of the plants, day temperatures ranged from 20° C. to about 22° C., night temperatures were about 18° C. and light levels ranged from 3,000 to 8,000 foot-candle. Plants were about 14 weeks old when the photographs and the description were taken. In the detailed description, color references are made to The Royal Horticultural Society Colour Chart, 2001 Edition, except where general terms of ordinary dictionary significance are used.

Botanical classification: *Ipomoea batatas* cultivar IP059.

Parentage:

*Female, or seed, parent.*—*Ipomoea batatas* cultivar Blackie, not patented.

*Male, or pollen, parent.*—A mixture of pollen collected from plants of the *Ipomoea batatas* cultivars Marguerite and Lady Fingers, both not patented.

Propagation:

*Type.*—By terminal cuttings.

*Time to initiate roots, summer.*—About seven days at temperatures of 24° C.

*Time to initiate roots, winter.*—About ten days at temperatures of 22° C.

*Time to produce a rooted young plant, summer.*—About 21 days at temperatures of 24° C.

*Time to produce a rooted young plant, winter.*—About 24 days at temperatures of 22° C.

*Root description.*—Fine to thick; white in color.

*Rooting habit.*—Freely branching; dense.

Plant description:

*Plant habit.*—Compact; mounding and outwardly spreading. Freely branching; about eight lateral branches per plant; pinching enhances lateral branch development.

*Plant height.*—About 11 cm.

*Plant diameter.*—About 30 cm.

Lateral branch description:

*Length.*—About 18 cm.

*Diameter.*—About 4 mm.

*Internode length.*—About 5 mm.

*Strength.*—Strong.

*Texture.*—Smooth, glabrous.

*Color.*—144C.

Foliage description:

*Arrangement.*—Alternate, simple.

*Length.*—About 9.5 cm.

*Width.*—About 7 cm.

*Shape.*—Roughly palmate with up to five lobes.

*Apex.*—Acute.

*Base.*—Cordate to hastate.

*Margin.*—Palmately-lobed.

*Texture, upper and lower surfaces.*—Smooth, glabrous.

*Venation pattern.*—Pinnate.

*Color.*—Developing and fully expanded foliage, upper surface; N144C; venation, 144B. Developing and fully expanded foliage, lower surface: 144D; venation, 144D.

*Petiole.*—Length: About 5 cm. Diameter: About 3 mm. Texture, upper and lower surfaces: Smooth, glabrous. Color, upper and lower surfaces: 145A.

Flower description:

*Flower arrangement and habit.*—Salverform flowers arranged singly or in clusters of five arising from leaf axils. Freely flowering habit with usually about 5 to 15 open flowers and flower buds per plant at a time. Flowers not persistent. Flowers not fragrant.

*Natural flowering season.*—Plants of the new Kalanchoe initiate and develop flowers under short day/long night conditions. Flower initiation and development can also be induced under artificial short day/long conditions (at least 14 hours of darkness).

*Flower longevity.*—Individual flowers last about 24 to 36 hours on the plant.

*Flower diameter.*—About 3 cm.

*Flower length (height).*—About 3 cm.

*Flower bud.*—Shape: Elongated oblong. Length: About 2 cm. Diameter: About 5 mm. Color: 75C.

*Corolla.*—Arrangement: Five petals fused at the base and opening into a flared trumpet. Petal length: About 3.2 cm. Petal width: About 1.5 cm. Petal shape: Roughly spatulate. Petal apex: Rounded. Petal margin: Entire. Petal texture, upper and lower surfaces: Smooth, velvety. Color: Petal, when opening, upper and lower surfaces: 76C. Petal, fully opened, upper and lower surfaces: 76C. Throat: 77B. Tube: 76C.

*Calyx.*—Arrangement: One single calyx tube per flower. Sepal shape: Lanceolate. Sepal apex: Acute. Color, upper and lower surfaces: Close to 144C.

*Reproductive organs.*—Stamens: Quantity/arrangement: Five per flower. Anther shape: Oval. Anther length: About 2 mm. Anther color: 155D. Pollen amount: Scarce. Pollen color: N155D. Pistils: Quantity: One per flower. Stigma shape: Oval. Stigma color: 155D. Ovary color: 155D. Seed/fruit: Seed and fruit development have not been observed on plants of the new *Ipomoea.*

Temperature tolerance: Plants of the new *Ipomoea* have been observed to tolerate temperatures from about 10° C. to about 38° C.

Pathogen/pest resistance: Plants of the new *Ipomoea* have not been observed to be resistant to pests and pathogens common to *Ipomoea.*

It is claimed:

1. A new and distinct *Ipomoea* plant named 'IP059' as illustrated and described.

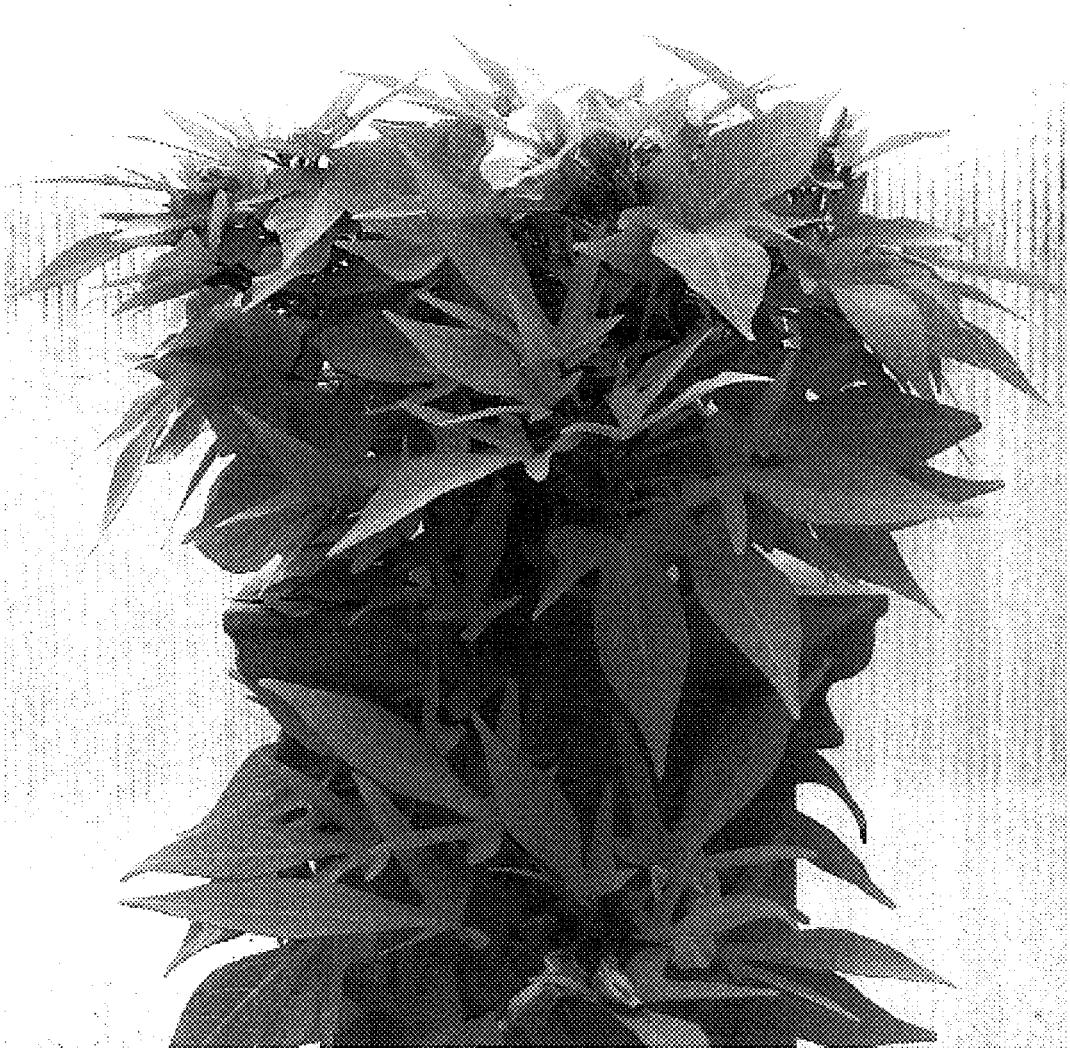

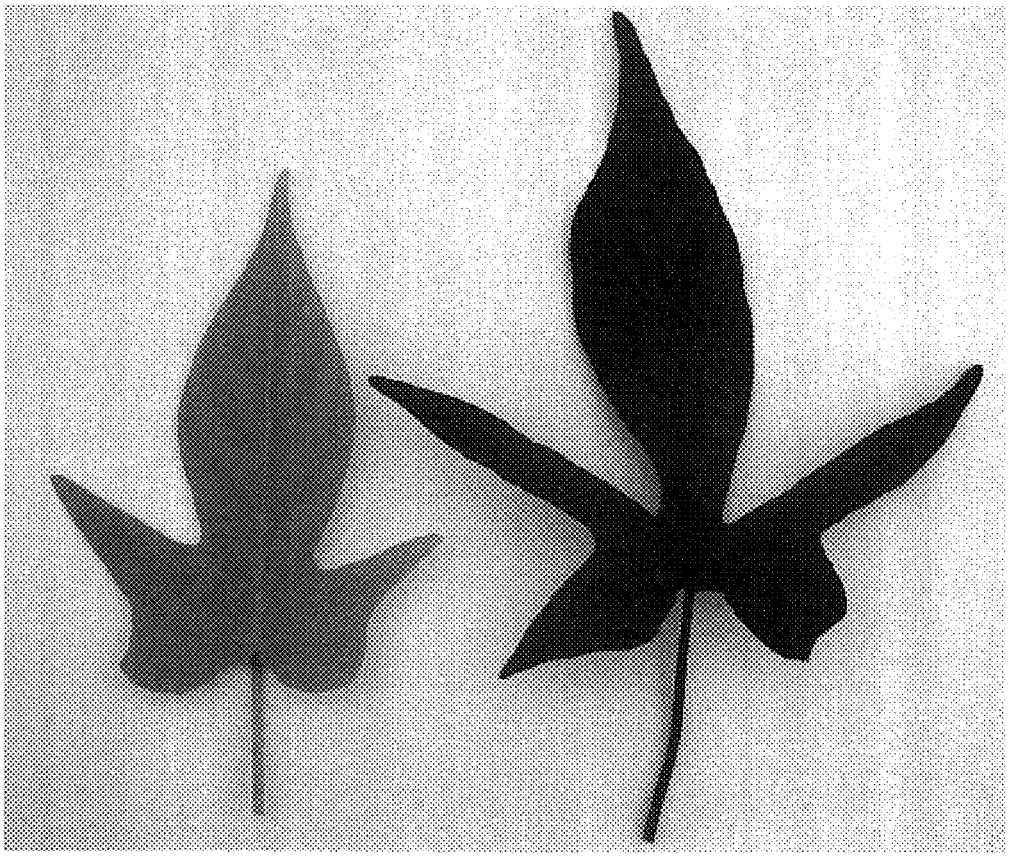

* * * * *